United States Patent [19]

Dryga et al.

[11] Patent Number: 5,035,142

[45] Date of Patent: Jul. 30, 1991

[54] METHOD FOR VIBRATORY TREATMENT OF WORKPIECES AND A DEVICE FOR CARRYING SAME INTO EFFECT

[76] Inventors: Alexandr I. Dryga, ulitsa marata, 6, kv.64; Nikolai A. Zadorozhny, ulitsa Dnepropetrovskaya, 141, both of Kramatorsk; Mikhail A. Kuzmin, ulitsa Avangardnaya, 15, kv.39, Moscow; Pavel M. Libman, Bolshe-Okhtinsky prospekt, 6, kv. 31, Leningrad, all of U.S.S.R.

[21] Appl. No.: 451,599

[22] Filed: Dec. 19, 1989

[51] Int. Cl.$^5$ .......................................... G01N 29/00
[52] U.S. Cl. ................................... 73/579; 148/12.9
[58] Field of Search .................. 73/579, 570, 573; 148/12.9

[56] References Cited

U.S. PATENT DOCUMENTS

| | | | |
|---|---|---|---|
| 3,622,404 | 11/1971 | Thompson | 148/12.9 |
| 3,677,831 | 7/1972 | Pezaris et al. | 73/579 |
| 3,741,820 | 6/1973 | Hebel, Jr. et al. | 148/12.9 |
| 4,381,673 | 5/1983 | Klauba et al. | 73/579 |
| 4,718,473 | 1/1988 | Musschoot | 148/12.9 |
| 4,823,599 | 4/1989 | Schneider | 73/579 |

FOREIGN PATENT DOCUMENTS 798185 1/1981 U.S.S.R. .

*Primary Examiner*—Hezron E. Williams
*Assistant Examiner*—Louis M. Arana
*Attorney, Agent, or Firm*—Fleit, Jacobson, Cohn, Price, Holman & Stern

[57] ABSTRACT

A method for vibratory treatment of workpieces involves repeatedly exiting a workpiece at its resonant frequencies of various harmonics by an unbalance vibration exciter connected to an electric motor. The race of one of the bearings of the motor armature is electrically insulated from the electric motor frame. The e.m.f. value of the bearing is measured continuously. Once the natural frequency of the workpiece being treated has been shifted as a result of the vibratory treatment performed, a change in the e.m.f. value is recorded and, after the natural frequency has been stabilized, the vibration exciter is retuned to the shifted value of the resonant frequency. The vibratory treatment is carried out on each harmonic until stabilization of the resonant frequency, at which time vibratory treatment on another harmonic is made. Multiply repeated vibratory excitation procedures on each of the harmonics are performed until a resonant frequency is reached, at which the e.m.f. value varies no longer.

5 Claims, 3 Drawing Sheets

METHOD FOR VIBRATORY TREATMENT OF WORKPIECES AND A DEVICE FOR CARRYING SAME INTO EFFECT

FIELD OF THE INVENTION

The invention relates to treatment of metal workpieces and is concerned more specifically with a method for vibratory treatment of workpieces and to a device for carrying same into effect.

The most effective field of application of the present invention is control over vibratory treatment of cast or welded workpieces aimed at reducing residual stresses therein.

Another field of application of the present invention can be control over vibratory treatment of workpieces after die-forging or bending in order to prevent their subsequent warping.

DESCRIPTION OF THE PRIOR ART

Welded or cast workpieces are liable to deformation under the effect of residual stresses as times goes by after their manufacture. Even in the course of their manufacture the dimensions of workpieces are likely to change to such a degree between their finishing and assembly that the dimensions of a finished product fail to satisfy requirements imposed thereon as for accuracy. Application of vibratory treatment enables one to stabilize geometric dimensions of a workpiece. The most efficient results of vibratory treatment are attainable due to the use of the resonance method, wherein the workpiece is treated at its resonant frequencies. Adequate efficiency of the resonance method is ensured due to high-amplitude vibratory stresses arising in the workpiece, which causes substantial reduction of residual stresses.

Equipment applied for vibratory treatment differs in the type of the vibration exciter used, a decisive parameter of which is the frequency range, and is classified into equipment incorporating unbalance (5 to 2000 Hz), electromagnetic (20 to 1000 Hz), and electrodynamic (5 to 5000 Hz) vibration exciters.

One of the important parameters characteristic of the vibration treatment conditions is time. A required treatment time is concerned first and foremost with the mass of the workpiece being treated. However, no particular duly substantiated recommendations on vibration treatment time occurs at the present time, since such time depends not only on the workpiece mass but also on its structural features, the level of residual stresses in the workpiece, and a number of other factors hardly taken account of. As a rule, the length of treatment time is determined empirically.

Known in the present state of the art is a method for vibratory reduction of internal stresses (U.S. Pat. No. 3,622,404), wherein a vibration exciter is made fast, through clamps, on the workpiece which is electrically insulated from the shop's floor, whereupon vibrations are excited therein. A device for carrying said method into effect is provided with an unbalance-type vibration exciter with a direct-current electric motor and has a vibration frequency regulator.

Prior to treatment of a workpiece there is performed vibratory scanning of the excitation frequency with a view to determine resonant frequencies. Once 6 to 12 resonant frequencies have been determined, vibration treatment is carried out at 4 to 6 of such frequencies. A symptom of reduction of residual stresses is a 10 to 15 percent drop of current consumed by the electric motor during vibratory treatment.

A disadvantage inherent in the aforesaid known method and in the device carrying said method into effect resides in too low an accuracy of determination of reduction of residual stresses and hence of the instant when the treatment is completed. Control over stabilization of residual stresses is effected immediately during the treatment process against the current consumed by the electric motor. However, the accuracy of measurement of a consumed current is affected by numerous factors concerned with energy losses, such as losses by internal friction in the material of the workpiece being treated, aerodynamic damping (loss by sound emission into the surrounding atmosphere, electric losses (by eddy currents and by heating the armature winding conductors), constructional damping at places of the vibrator-to-workpiece contacts, as well as losses in shock-absorbers on which the workpiece is positioned. The aforelisted energy losses are liable to change within broad limits under the effect of extrinsic uncontrollable factors. The energy consumed for reduction of residual stresses is measured against a background of the total energy losses which exceed the amount of energy spent for reduction of residual stresses.

The closest to the method disclosed herein is a method for vibratory treatment of workpieces (SU, A, 798,185) with the aid of an electromechanical unbalance vibration exciter connected to an electric motor. The known method makes provision for multiply repeated vibratory excitation of the workpiece being treated at resonant frequencies of the various harmonics, followed by taking down vibratory displacements and vibromotive forces applied, finding out the amplitude-phase-frequency characteristic of vibratory excitation of the workpiece involved, determining the real part of the amplitude-phase-frequency characteristic, and completing the treatment as soon as the zero-crossing points of said characteristic discontinue shifting, which corresponds to stabilization of the workpiece vibration frequency and hence to stabilization of residual stresses.

A disadvantage inherent in the known method resides in a low accuracy of determination of the kinetics of variation of residual stresses and their stabilization, since the amplitude-phase-frequency characteristic of vibratory excitation is affected by the signals of adjacent harmonics, noises interferences and unaccounted vibrations.

A prior-art device for carrying into effect the afore-discussed method for vibratory treatment of workpieces (SU, A, 798,185) is known to comprise an electromechanical unbalance vibration exciter connected to a variable-speed electric motor, a voltage converter, a measuring instrument, two filters, a transducer of vibratory displacements of the workpiece being treated, connected to the input of the first filter, a multiplier, a measuring instrument, a force cell serially connected, via the second filter, to the first input of the multiplier whose second input is connected to the output of the first filter and the output, to the measuring instrument.

In the course of operation the vibration exciter sets up mechanical vibrations in the workpiece being treated, the workpiece excitation frequency being varied in order to attain its tuning to resonance. The excitation frequency is varied by means of the voltage converter. The force cell is located at the output of the vibration exciter and is adapted to generate an electric signal proportionate to the excitation force. Distortions of the excitation force pulse are rejected by the second filter. Reaction of the workpiece to the excitation applied thereto is measured, as its vibratory displacement, by the vibratory displacement transducer with due account of the phase of the vibratory displacement signal with respect to the excitation force signal, the distortions of the vibration displacement signal being rejected by the first filter. Then the amplitude-phase-frequency characteristic is established proceeding from the presentation given by the transducers, the real part of the above characteristic is determined as well as the points of crossing of the real part of the amplitude-phase-frequency characteristic of vibratory excitation through zero axis, and as soon as said crossing points cease shifting the vibration treatment process is terminated.

A disadvantage inherent in said device lies with the absence of stabilization of the motor speed and of the vibration exciter rate. This is liable to disturb conditions of resonance, distort the amplitude-phase-frequency characteristic of vibratory excitation and impede registration of the kinetics of variation of residual stresses and their stabilization.

OBJECTS AND SUMMARY OF THE INVENTION

It is an object of the present invention to enhance the efficiency of vibratory treatment of workpieces.

It is another object of the present invention to provide higher accuracy of measurement of the resonant frequency concerned with the kinetics of variation of residual stresses.

It is one more object of the present invention to provide higher accuracy of registration of an instant when final stabilization of residual stresses in the workpiece occurs.

It is a further object of the present invention to save energy spent for vibration treatment of the workpiece being handled and to curtail the workpiece treatment time.

It is still one more object of the present invention to provide a possibility of full automation of the vibratory treatment process of a workpiece.

It is yet still one more object of the present invention to provide higher output of the vibration exciter.

The foregoing and further objects are accomplished due to the fact that in method for vibratory treatment of workpieces, consisting in multiply repeated vibratory excitation of the workpiece being treated at its resonant frequencies of the various harmonics with the aid of an electromechanical unbalance vibration exciter connected to an electric motor, till stabilization of the resonant frequencies, according to the invention, the value of the electromotive force of the electric motor armature bearing is continuously measured in the course of the vibratory treatment, once the e.m.f. value has ceased changing, the vibration exciter is tuned to resonance in the natural frequency of the workpiece that has been shifted as a result of the vibratory treatment and multiply repeated vibratory excitation is carried out on each of the harmonics till reaching a frequency at which the e.m.f. remains invariable.

The development mechanism of the e.m.f. in the bearings of electric motors is based on the phenomenon of the e.m.f. induction in case of a nonsymmetrical magnetic flux in the magnetic system of a circuit consisting of a shaft, a bearing and an electric motor frame. The electric motor armature shaft runs in bearings, wherein a hydrodynamic oil film is formed, whose electrical resistance varies depending on the electric motor operating duty. When the bearing is electrically insulated from the electric motor frame an e.m.f. can be detected across the electric terminals of the motor frame and the bearing race. The condition of the hydrodynamic oil film depends on the reaction of the workpiece being treated, which is translated via the vibration exciter to the shaft of the electric motor armature, while the e.m.f. value is drastically increased in the resonant mode.

It is due to the e.m.f. of the bearing that one can register the force of vibratory effects uninterruptedly.

A signal informing on the e.m.f. value in the bearing is emplyed for control of the vibratory treatment process.

Treatment of workpiece in the resonant mode of vibratory forces in the bearing makes it possible to take account of a current change in the resonant frequency due to the kinetics of residual stresses.

Termination of the treatment procedure upon discontinuation of the e.m.f. changes in the bearing provides for high-accuracy registration of the instant of final stabilization of residual stresses in the workpiece being treated.

Vibratory treatment is carried out in a resonant mode at a stabilized vibration rate at which energy put in the workpiece and absorbed by it ensures maximally a considerable saving of energy consumed due to a shorter lapse of time within which residual stresses in the workpiece are reduced.

Registration of the instant of final stabilization of residual stresses in the workpiece and termination of the treatment procedure make it possible to exclude the time of unproductive vibratory effects past stabilization of residual stresses.

According to one of the embodiments of the invention vibratory treatment is discontinued in the course of tuning of the vibration exciter. Such an embodiment of the invention makes it possible to use relatively simple equipment for carrying the method of the invention into effect.

According to a preferred embodiment of the invention vibratory treatment is conducted continuously within the entire process of vibratory effects.

Such an embodiment of the invention enable one to completely automate the process of vibratory treatment of workpieces.

The aforesaid object is accomplished also due to the fact that in a device for vibratory treatment of workpieces, comprising an electromechanical unbalance vibration exciter connected to a variable-speed electric motor, a voltage converter and a measuring instrument, according to the invention, provision is also made therein for an amplifier, an automatic electric motor speed stabilization unit, and an electric motor angular speed pickup, the race of one of the bearings of the electric motor armature is electrically insulated from the electric motor frame, the input of the automatic electric motor speed stabilization unit is connected, through the electric motor angular speed pickup and a commutator, to the electric motor armature winding, whereas the output of the electric motor speed stabilization unit is connected to the converter input, and the measuring instrument is connected to the amplifier output, the amplifier input being connected to the electric motor frame and to the race of the electric motor armature bearing.

In a preferred embodiment of the invention provision is made for a setter of intensity of the input voltage variation of the automatic electric motor speed stabilization unit and for a computing unit, the input of the automatic speed stabilization unit being connected, via the setter, to the computing unit, which in turn is connected to the measuring instrument in order to print out data on the vibratory treatment process of the workpiece involved, and to the amplifier output.

Such an embodiment of the present invention is efficient for complete automation of the vibratory treatment process of workpiece.

BRIEF DESCRIPTION OF THE DRAWINGS

Further objects and advantages of the present invention will become more apparent from a consideration of the following detailed description of some specific exemplary embodiments thereof and the accompanying drawings, wherein.

DETAILED DESCRIPTION OF THE PREFERRED EMBODIMENTS

The method for vibratory treatment of workpieces, according to the invention, is outlined in the following. The workpiece being treated, wherein residual stresses are present, is subjected to vibratory excitation with the aid of an electromechanical unbalance vibration exciter connected to an electric motor, said vibratory excitation of the workpiece being effected at its resonant frequencies on the various harmonics. The e.m.f. value of the electric motor armature bearing is measured continuously in the course of the vibratory treatment process. A change in the e.m.f. value results from a reduction of residual stresses in the workpiece due to vibratory treatment thereof. At each of the treatment stages one should retune the vibratory excitation frequency on a preset harmonic so as to provide resonance at the workpiece natural frequency that has been shifted as a result of vibratory treatment, making use of a signal of a change in the e.m.f. value. Once the e.m.f. value has ceased changing on each of the harmanics, the vibration exciter is tuned in the frequency of an adjacent harmonic. Vibratory excitation is repeated many times in succession stage-by-stage until a frequency is reached at which the e.m.f. value changes no longer.

The vibration exciter is tuned in the frequency of an adjacent harmonic either at the interval between the stages of the treatment at different harmonics or automatically in the course of continuous vibration treatment of the workpiece.

Figure 1:
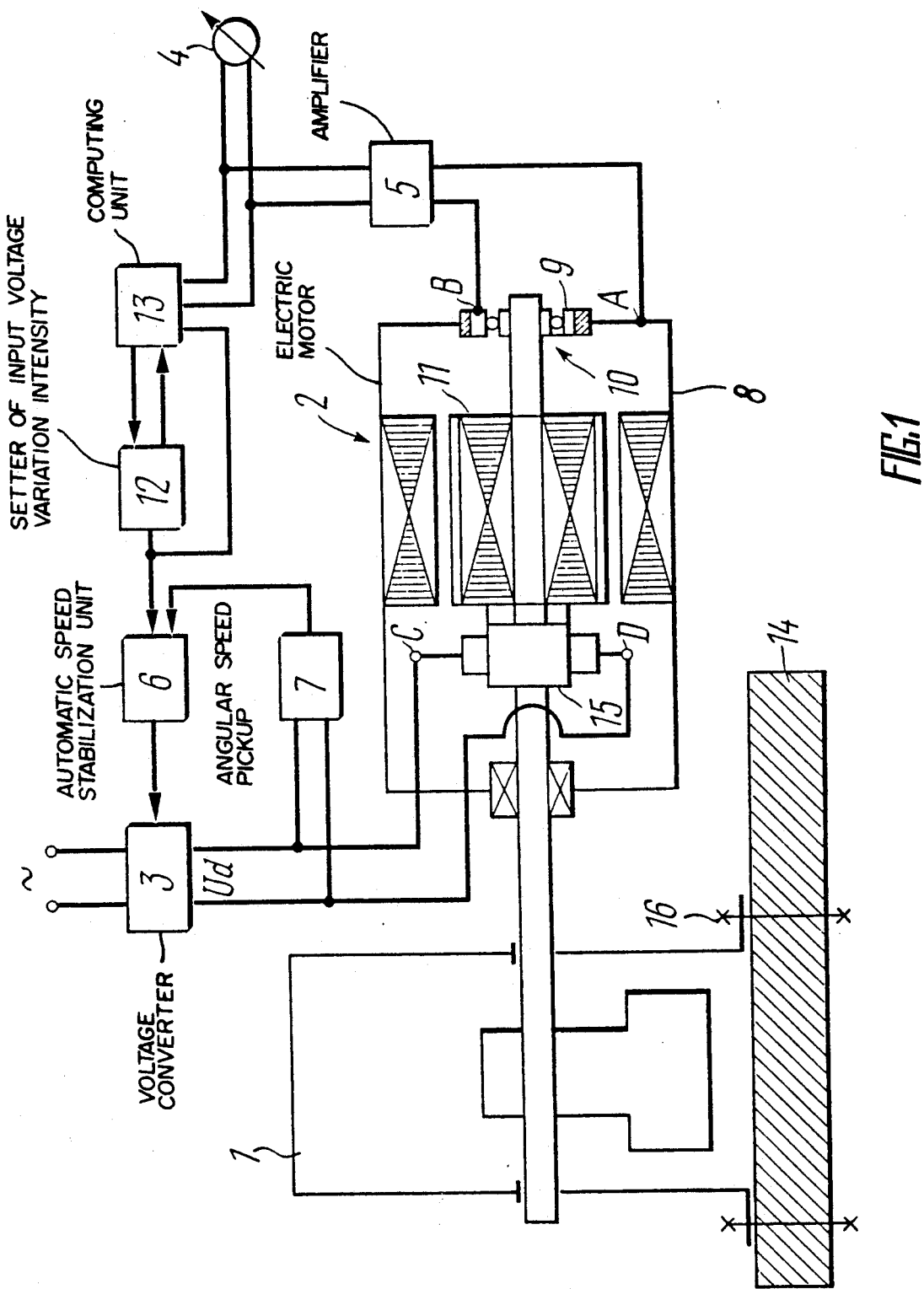
FIG. 1 is a schematic view of a device, according to the invention.

The device for carrying the method for vibratory treatment of workpieces into effect comprises an electromechanical unbalance vibration exciter 1 (FIG. 1) connected to a variable-speed electric motor 2, a voltage converter 3, a measuring instrument 4, an amplifier 5, a unit 6 of automatic speed stabilization of the electric motor 2, a pickup 7 of angular speed of the electric motor 2, wherein a race 9 of one of bearings 10 of its armature 11 is electrically insulated from a frame 8 of the electric motor 2, a setter 12 of intensity of the input voltage variation of the unit 6 of automatic speed stabilization of the electric motor 2, and a computing unit 13. The input of the automatic speed stabilization unit 6 is connected, through the setter 12, to the computing unit 13, which in turn is connected to the measuring instrument 4 in order to print out data on the workpiece vibratory treatment process, and to the output of the amplifier 5 and is also connected, through the pickup 7 of angular speed of the electric motor 2 and a commutator 15, to the winding of the armature 11 of the electric motor 2, while the output of the unit 6 is connected to the input of the converter 3. The measuring instrument 4 is connected to the output of the amplifier 5 whose input is connected, through a terminal A, to the frame 8 of the electric motor 2 and, through a terminal B, to the race 9 of the bearing 10 of the armature re 11 of the electric motor 2.

The direct-current electric motor 2 is powered from the converter 3 of electric voltage in the capacity of which is used a controlled rectifier adapted to rectify commercial-frequency alternating-current voltage and a wide-range control of the rectified voltage $U_d$ of direct (pulsating) current. The controlled rectifier is built around thyristors according to a full-wave centre-tap circuit. The thyristors are powered from a power transformer, which effects decoupling of the electric motor circuits from power mains and steps mains voltage down to a level safe as for the operating conditions specified.

The pickup 7 is used for measuring a current value of the angular speed $\Omega$ of the electric motor 2. Under constant magnetic flux of the electric motor 2 its speed is measured with the aid of a tachometric bridge rather than by means of a tachogenerator. An electromotive force T is induced across the terminals C and D of the winding of the armature 11 of the electric motor 2, said force T being determined from the relationship:

$$F = b \cdot F \cdot \Omega,$$

where
b—electric motor constant;
F—magnetic flux;
$\Omega$—angular rotation speed of the electric motor 2.

The input of the pickup 7 is connected to the terminals C and D of the electric motor 2. Voltage picked off the output of the pickup 7, is proportional to the value of T and hence to the speed $\Omega$ of the electric motor 2 under steady-state conditions.

Application of the pickup 7 for measuring the rotation speed of the electric motor 2 instead of a conventionally employed tachogenerator simplifies the construction of the electromechanical exciter and makes its operation more reliable.

The unit 6 of automatic stabilization of the speed of the electric motor 2 maintains a preset rotation speed of the electric motor 2 in cases of such extrinsic disturbing factors as fluctuation of alternating-current mains voltage, changes in the condition of the lubricant in the electric motor 2, change in mechanical and electrical losses in electric motor 2. Application of a negative feedback makes it possible to provide linear characteristics of the converter 3, which in turn extends the range of the speed control of electric motor 2.

Figure 2:
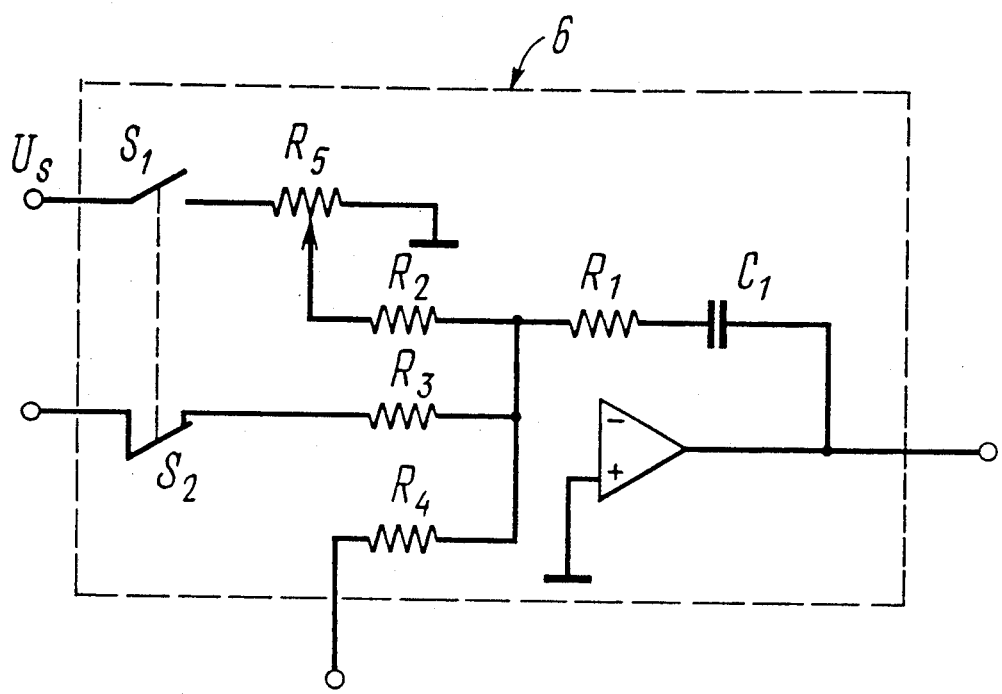
FIG. 2 is an alternative embodiment of the automatic electric motor speed stabilization unit, according to the invention.

The unit 6 is in fact a proportional-pluse-integral controller and a discrete speed setting subunit (FIG. 2).

The controller is based on an operational amplifier, which incorporates in its feedback circuit a resistor $R_1$ and a capacitor $C_1$. The controller feedback is effected by resistors $R_2$, $R_3$ of the speed setting circuits and by a resistor $R_4$ in the speed feedback circuit of the electric motor 2. The speed setting subunit is in effect a variable resistor $R_5$ connectable to a voltage $U_s$ of a source of stabilized direct current through a switch $S_1$. The slider of the resistor $R_5$ is connected to the resistor $R_2$.

The setter 12 of intensity of the input voltage variation of the unit 6 is connected to the resistor $R_3$ through a switch $S_2$ mechanically interlocked with the switch $S_1$ so that when the switch $S_2$ is closed the switch $S_1$ is open and, vice versa, with the switch $S_1$ closed the switch $S_2$ is open.

The setter 12 of intensity of the input voltage variation of the unit 6 is adapted for converting stepwise variation of the voltage from the output of the computing unit 13 into a voltage varying linearly with time and set at the unit 6. The level of the output voltage from the computing unit 13 after having been reproduced by the intensity setter 12 reaches the level of the input voltage of the unit 6. Linear variation of the voltage setter 12 from the zero to the maximum value enable the electric motor 2 to be speeded up with a constant acceleration, thereby realizing the range of vibration frequencies defined by the rotation speed of the electric motor 2.

Application of the setter 12 facilitates conduction of vibratory treatment at the natural frequencies of the workpiece 14 being treated and enables automation of the vibration treatment process.

The computing unit 13 makes it possible to automate the process of vibratory treatment of the workpiece 14 and provides for flexible programmed control over the technological process of vibratory treatment.

The unit 13 incorporates all principal routine elements inherent in any computing system, i.e., an arithmetic-logical device, a memory device, an input-output device, and a control device.

The input-output device establishes communication between the unit 13 and the setter 12 and, via the amplifier 5, with the terminal A on the frame 8 of the electric motor 2 and with the terminal B of the bearing 10 electrically insulated from the frame 8 of the electric motor 2.

The memory device is used for storing of programs and recording of information on the value of the bearing e.m.f., which arrives from the bearing 10 electrically insulated from the frame 8 of the electric motor 2, through the amplifier 5 and is applied to the unit 13, as well as on the value of the output voltage of the setter 12.

The control unit is adapted for decoding the commands recorded in a program and generates signals for the computing unit to function.

For drawing up documents concerning with the technological of vibratory treatment of the workpiece 14 the resonant frequencies of vibratory excitation are printed out and taken down by a recorder (omitted in the Drawing) connected to the measuring instrument 4.

A direct-current electric motor powered from the voltage converter 3 is used as the electric motor 2. The output of the converter 3 is connected to the winding of the armature 11 of the electric motor 2 through the terminals C and D of the commutator 15. The electric motor 2 has separate excitation.

Figure 3:
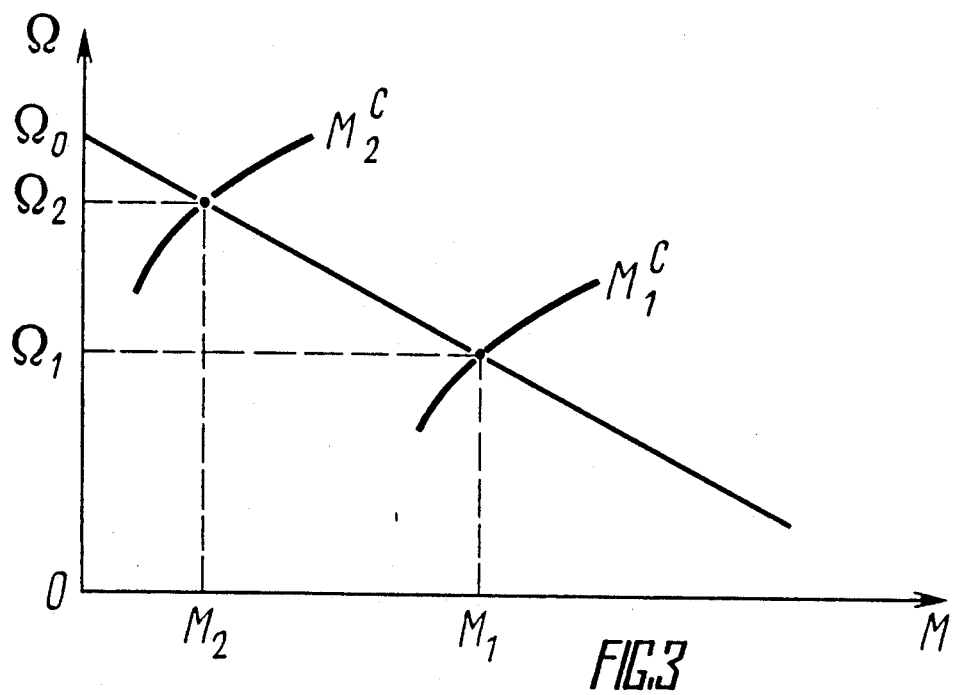
FIG. 3 presents an electromechanical characteristic of the vibration exciter, according to the invention.

When substantiating the operating conditions of the electric motor 2 and making an analysis into the conditions for its stable operation in combination with the vibration exciter 1, use is made of a relationship between the speed $\Omega$ of the electric motor 2 and the torque M on the shaft thereof. The mechanical characteristic of the electric motor 2 varies linearly (FIG. 3) with respect to the value of $\Omega_0$, i.e., a no-load angular speed of the electric motor 2. Under steady-state conditions with $\Omega = \Omega_1$ the value of the torque M on the shaft of the electric motor 2 equals the value of the antitorque moment $M_1{}^c$, that is, $M_1 = M_1{}^c$.

The value of the antitorque moment $M_1{}^c$ depends on the amount of a vibratory force resulting from rotation of the shaft of the vibration exciter 1 secured on the workpiece 14.

When the frequency of vibratory excitation equals one of the natural frequencies of the workpiece 14 being treated, resonance sets in, and the vibratory force $M_1{}^c$ acquires its maximum value. When a deviation from resonance occurs the value of the vibratory force $M_1{}^c$ decreases and hence the antitorque moment, during the motor shaft rotation, gets lower than the value of $M_2$, while the angular speed of the electric motor 2 rises up to the value of $\Omega = \Omega_2$.

A decrease in the natural frequency of the workpiece being treated due to vibratory treatment results in a reduction of the e.m.f. value.

Prior to commencing vibratory treatment of the workpiece 14 one should determine its resonant frequencies. Then the speed values of the electric motor 2 corresponding to said resonant frequencies, are entered into the memory of the computing unit 13.

For carrying out vibratory treatment the vibration exciter is to be fixed in place on the workpiece 14 being treated with the aid of the clamps 16. Then the rotation speed of the electric motor 2 is changed so as to attain a mechanical resonance, i.e., a vibratory effect is exerted in such a manner that the vibratory excitation frequency (as set by the rotation speed of the electric motor 2) should get equal to one of the resonant frequency of the workpiece 14.

Vibratory treatment is effected at a constant rate of vibratory effects. To this effect use is made of the speed setter 12. The value voltage variation across the pickup 7 is substrated in the automatic speed stabilization unit 6 from the value of the voltage across the setter 12, whereby a negative feedback with respect to the speed of the electric motor 2 is ensured.

Figure 4:
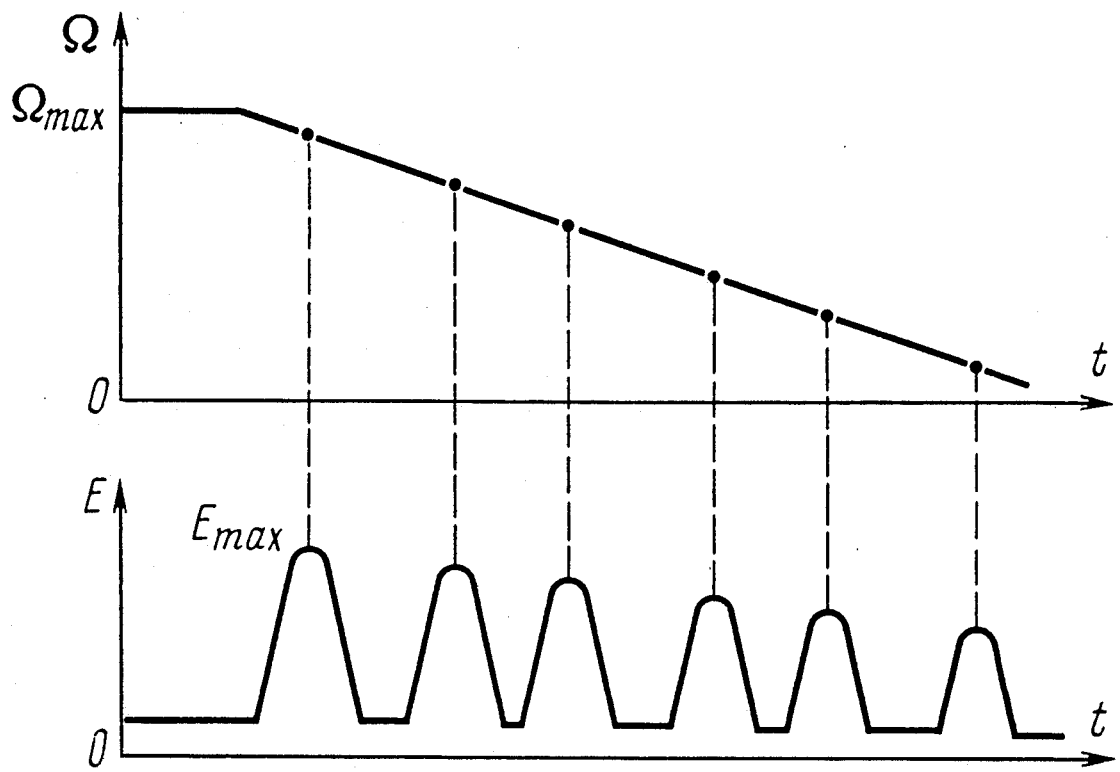
FIG. 4 depicts a frequency-and-amplitude characteristic of the e.m.f. variation with due account of resonance on the various harmonics, according to the invention.

FIG. 4 shows a graphic representation of the nature of the process of vibratory effects. The electric motor 2 is speeded up with constant acceleration so that the angular speed $\Omega$ of the electric motor 2 rises up to its maximum value $\Omega_{max}$. As soon as the vibratory excitation frequency falls in coincidence with one of the resonant frequencies of the workpiece 14 the e.m.f. of the bearing 10 reaches its maximum value $E_{max}$.

The initial vibratory excitation is carried out either at the lowest or at the highest natural frequency of the workpiece 14 within the preselected frequency range.

In the course of vibratory excitation microplastic deformations are liable to occur in the material of the workpiece 14, with the result that the internal residual stresses therein are reduced and get stabilized during further treatemtn. Such changes in the residual stresses in the workpiece 14 resulting from vibratory excitation lead to a change in the resonant frequency of the workpiece 14.

Figure 5:
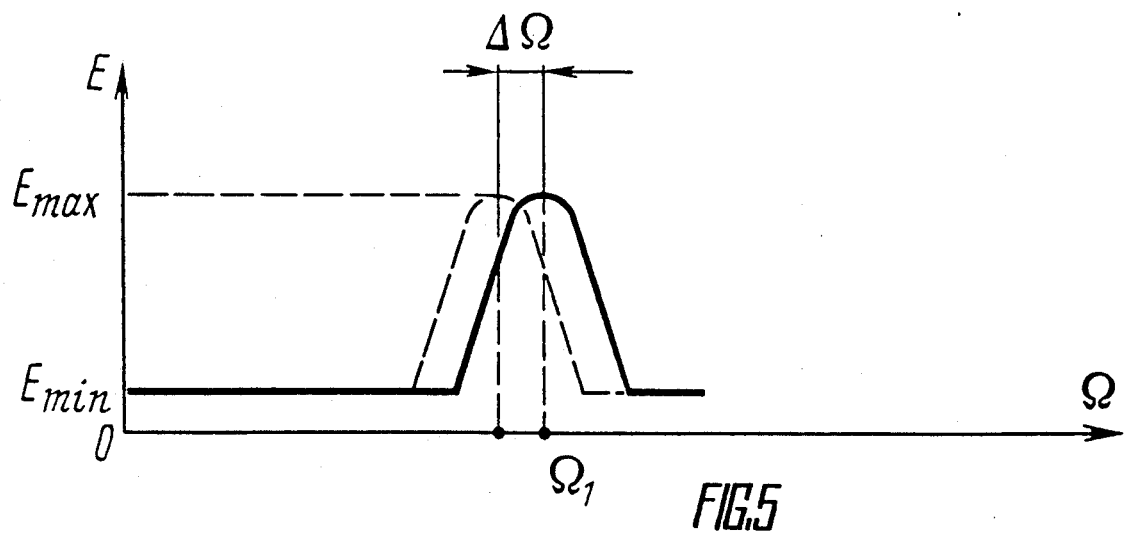
FIG. 5 represents an amplitude-frequency characteristic of the e.m.f. and its shifting due to vibratory excitation.

FIG. 5 illustrates the process of vibratory excitation at one of the resonant frequencies of the workpiece 14. With vibratory excitation carried out at the resonant frequency $\Omega_1$ (indicated with a solid line in the graphic chart) the e.m.f. of the bearing 10 reaches its maximum value $E_{max}$. As a result of such vibratory excitation at said frequency microplastic deformations in the material of the workpiece 14 occur, internal residual stresses are reduced, the e.m.f. value of the bearing 10 drops, and the resonant frequency of the workpiece 14 is shifted towards the lower-frequency region. The value of $\Delta\Omega$ is characteristic of a resonant frequency drift as a result of partial reduction of the internal residual stresses in the workpiece being treated. The e.m.f. of the bearing 10 acquires its maximum value this time at a frequency of vibratory excitation that has been shifted as a result of vibratory treatment (indicated with a dotted line in the graphic chart). In the case of incoincidence of the vibratory excitation frequency with one of the resonant frequencies of the workpiece 14 the e.m.f. of the bearing 10 has a lower value, i.e., $E \rightarrow E_{min}$.

The process of vibratory treatment is effected in an automatic continuous mode. Upon initial vibratory loading of the workpiece 14 on a preset harmonic, there is carried out, as a result of operation of the unit 6, an automatic tuning to resonance till stabilization of the e.m.f. value of the bearing 10. Then the computing unit 13 sends a command to change to an adjacent harmonic featured by another resonant frequency. Then tuning to resonance is also performed at this new stage till stabilization of the e.m.f. value of the bearing 10. Vibratory treatment is discontinued as soon as the e.m.f. value of the bearing 10 remains constant after changing over to an adjacent harmonic.

A simplified version of the method proposed herein can be carried into effect without the use of the setter 12 and the computing unit 13.

In such a case vibratory treatment of the workpiece 14 is interrupted and the vibration exciter 1 is retuned with the aid of the unit 6 in a discrete mode.

Next the e.m.f. value of the bearing 10 is read off the measuring instrument 4 and vibratory excitation continues at a given frequency till stabilization of the e.m.f. value, i.e., when the minimum value of the e.m.f. of the bearing 10, as read by the instrument 4 does not change, vibratory excitation is discontinued, whereupon retuning in the frequency that has been shifted as a result of partial relieving of internal stresses in the workpiece 14 is carried out and vibratory effects are repeated. Vibratory excitation on a given harmonic is discontinued whenever the e.m.f. value does not change after a next retuning of the vibration exciter 1 to resonance and remains at its maximum. This very instant is in fact the point of final stabilization of internal stresses in the workpiece 14 on a given harmonic. As a result, microplastic deformations in the material of the workpiece 14 cease, as well as vigorous absorption of the energy of vibrations by the workpiece 14. Thereupon vibratory excitation of the workpiece 14 at another resonant frequency is carried out, followed by similar vibratory excitation procedures at other resonant frequencies of the workpiece 14.

The process of vibratory treatment is terminated whenever no reduction of the e.m.f. value occurs as a result of vibratory excitation at other resonant frequencies of the workpiece 14, which is registered against the instrument 4.

What is claimed is:

1. A method for vibratory treatment of workpieces, comprising the steps of:
   providing an electric motor and an electromechanical unbalance vibration exciter connected to said electric motor, said electric motor including an armature bearing race and an electric motor frame, said armature bearing race being electrically insulated from the electric motor frame;
   exiting repeatedly a workpiece being treated, so as to vibrate the workpiece at resonant frequencies of various harmonics, by said electromechanical unbalance vibration exciter;
   measuring an e.m.f. value of the electric motor between said armature bearing race and the electric motor frame continuously in the course of vibratory excitation of the workpiece at a resonant frequency of one harmonic of the workpiece;
   tuning said vibration exciter to resonance at the resonant frequency of said workpiece, after said resonant frequency has been shifted due to said vibratory excitation, by changing a speed of rotation of the electric motor;
   stabilizing the resonant frequency of said workpiece;
   discontinuing the vibratory excitation at said harmonic when stabilization of the resonant frequency, at which the e.m.f. value changes no longer, is reached; and
   changing over to vibratory treatment of said workpiece at an adjacent harmonic.

2. A method as claimed in claim 1, wherein the vibratory excitation is discontinued during tuning of said vibration exciter.

3. A method as claimed in claim 1, wherein the vibratory excitation is carried out continuously throughout the vibratory treatment.

4. A device for vibratory treatment of workpieces, comprising:
   an electromechanical unbalance vibration exciter;
   a variable-speed electric motor connected to said vibration exciter, said motor carrying out vibratory excitation of a workpiece at resonant frequencies of various harmonics, said electric motor including a frame and an armature with a commutator;
   bearings for supporting said armature, one of said bearings including a race electrically insulated from said frame, an e.m.f. being induced between the race, insulated from the frame, and the frame;
   a unit for producing automatic stabilization of the speed of said electric motor and adapted to eliminate effects of extrinsic disturbing factors;
   an angular speed pickup for measuring current values of an angular speed of said electric motor;
   an amplifier for amplifying the induced e.m.f.;
   a measuring instrument for measuring an amplified e.m.f.;
   a voltage converter for producing controlled d.c. voltage and power supply to said electric motor;
   wherein an input of said unit for producing automatic stabilization of the speed of said electric motor is connected, through said angular speed pickup and said commutator, to a winding of said armature, an output of said unit is connected to an input of said voltage converter, said measuring instrument is connected to an output of said amplifier and an input of said amplifier is connected to said frame of the electric motor and to said race of the one of the bearings for supporting said armature.

5. A device as claimed in claim 4, and further comprising a setter for setting the intensity of input voltage variation of said unit for producing automatic stabilization and a computing unit, wherein the input of said unit for producing automatic stabilization is connected, through said setter, to the computing unit, and the computing unit, in turn, is connected to said measuring instrument for printing out data on the vibratory treatment of said workpiece, and to the output of said amplifier.

* * * * *